United States Patent
Muhlhoff et al.

(10) Patent No.: US 7,784,944 B2
(45) Date of Patent: Aug. 31, 2010

(54) METHOD AND DEVICE FOR DETERMINING MOVEMENT OF A HUMAN EYE

(75) Inventors: Dirk Muhlhoff, Kunitz (DE); Mario Gerlach, Neuendorf (DE)

(73) Assignee: Carl Zeiss Meditec AG, Jena (DE)

( * ) Notice: Subject to any disclaimer, the term of this patent is extended or adjusted under 35 U.S.C. 154(b) by 701 days.

(21) Appl. No.: 10/560,475

(22) PCT Filed: Jun. 7, 2004

(86) PCT No.: PCT/EP2004/006135

§ 371 (c)(1),
(2), (4) Date: Jun. 5, 2006

(87) PCT Pub. No.: WO2004/110261

PCT Pub. Date: Dec. 23, 2004

(65) Prior Publication Data

US 2006/0279698 A1    Dec. 14, 2006

(30) Foreign Application Priority Data

Jun. 12, 2003 (DE) ............................... 103 26 527

(51) Int. Cl.
*A61B 3/14* (2006.01)
(52) U.S. Cl. ..................................... 351/209
(58) Field of Classification Search .......... 351/208–209
See application file for complete search history.

(56) References Cited

U.S. PATENT DOCUMENTS

| | | | |
|---|---|---|---|
| 5,442,412 A | 8/1995 | Frey et al. | |
| 5,659,327 A * | 8/1997 | Furness et al. | 345/8 |
| 5,682,224 A * | 10/1997 | Takagi et al. | 351/208 |
| 5,847,827 A * | 12/1998 | Fercher | 356/493 |
| 6,210,401 B1 | 4/2001 | Lai | |
| 6,755,819 B1* | 6/2004 | Waelti | 606/5 |
| 2002/0013573 A1 | 1/2002 | Telfair et al. | |
| 2004/0021874 A1* | 2/2004 | Shimmick | 356/497 |
| 2006/0206102 A1* | 9/2006 | Shimmick | 606/4 |

FOREIGN PATENT DOCUMENTS

| | | |
|---|---|---|
| DE | 195 07 036 A1 | 9/1996 |
| DE | 102 07 535 A1 | 9/2003 |
| EP | 1 252 872 A1 | 10/2002 |

* cited by examiner

*Primary Examiner*—Joseph Martinez
*Assistant Examiner*—James R Greece
(74) *Attorney, Agent, or Firm*—Patterson Thuente Christensen Pedersen, P.A.

(57) ABSTRACT

A device for determining a movement of an eye includes an illumination unit by which optical radiation can be generated and emitted as an illumination ray bundle for illumination of at least one area of the cornea of the eye, a distance-determining unit, by which the illumination ray bundle returned as a detection ray bundle by the cornea can be received in a temporally resolved manner. A distance signal corresponding to a distance of the cornea from a reference plane can be generated using the received optical radiation of the detection ray bundle. the reference plane is defined relative to the distance-determining unit, and an evaluating unit, by which a position or movement signal corresponding to a position or movement of the eye can be generated using the distance signal.

30 Claims, 9 Drawing Sheets

METHOD AND DEVICE FOR DETERMINING MOVEMENT OF A HUMAN EYE

FIELD OF THE INVENTION

The present invention relates to a method and a device for determining movement of a human eye, wherein the cornea of the eye is irradiated with optical radiation.

BACKGROUND OF THE INVENTION

In ophthalmology, different methods have been developed for treating a visual deficiency in a patient by modifying the cornea of the patient's eye concerned. For instance, by means of laser radiation, the curvature of the cornea of a human eye can be selectively modified. Examples include known methods referred to by the acronyms LASIK, PRK and LASEK. In these methods, a treatment laser beam is passed, in a scanning mode, over the pupil area to be corrected, said laser beam thus causing a modification of the cornea. This modification of corneal geometry has to be effected at determined positions relative to the visual axis of the eye so as to allow said visual deficiency to be improved or removed.

However, during the treatment period, the eye executes a multiplicity of voluntary and involuntary movements, e.g. saccades, microsaccades, torsional movements, etc., which are accompanied by a corresponding movement of the visual axis. However, during treatment, such movements prevent precise alignment of the treatment laser beam relative to the visual axis.

Various methods are used to reduce or to prevent such deviations.

A first class of methods attempts to completely suppress any movements of the eye. For this purpose, for example, so-called applanation objects, e.g. plates or curved contact glasses, which are connected to the treatment device, can be employed, which are retained on the front section of the eye by mechanical pressure and/or vacuum. Due to the mechanical coupling of the eye with the treatment device, the eye movement relative to the treatment device is suppressed. Therefore, the treatment laser beam can be precisely aligned relative to the visual axis of the eye. However, the use of such applanation objects is, in many cases, undesired.

In a second class of methods, the effects of the eye movement on the alignment of the treatment laser beam relative to the visual axis are compensated for by selective and near-simultaneous re-direction of the treatment laser beam according to the eye movement. This requires detection of the movement of the eye.

In most cases, the detection of movement is based on video detection of the front eye section and subsequent digital image processing and evaluation. This allows detection of typical characteristics of the eye, e.g. the pupil rim or the transition between the iris and the sclera, and determination of their movement and position.

In further methods for the detection of movement, the pupil rim, the sclera boundary or artificially applied marks, as in EP 125 28 72, are scanned.

From the determined position and movement data, a compensation signal is then generated, which is used for positioning the treatment laser beam.

However, the video-based methods have the disadvantage that the movement and position signals are generated at insufficient speed or frequency, respectively. Said methods do not allow tracking of rapid eye movements, so that, where high precision is required for aligning the treatment laser beam relative to the visual axis of the eye, considerable deviations may occur between the desired position of the treatment laser beam and the actual position of the treatment laser beam relative to the visual axis of the eye.

Moreover, movement of the eye is only detected in two spatial dimensions, which are essentially perpendicular to the visual axis of the eye.

Therefore, it is an object of the present invention to provide a method and a device for determining eye movement, said method or device allowing quick, high-precision determination of the eye movement.

SUMMARY OF THE INVENTION

The object is achieved by a method of determining a movement of an eye, wherein optical radiation is irradiated onto the cornea of the eye as an illumination ray bundle, distance signals according to the distance of the cornea from a predetermined reference plane are generated in a temporally resolved manner by using the optical radiation returned by the cornea as a detection ray bundle, and position or movement signals are generated from said distance signals corresponding to a position or movement of the eye.

The object is further achieved by a device for determining a movement of an eye with an illumination device, which generates optical radiation during operation and emits said radiation as an illumination ray bundle for illumination of at least one area on the cornea of the eye, said device comprising a distance-determining unit, which, in a temporally resolved manner, receives the illumination ray bundle returned by the cornea as a detection ray bundle and, using the received optical radiation of the detection ray bundle, generates a distance signal corresponding to a distance of the cornea from a reference plane which is defined relative to the distance-determining unit, and comprising an evaluating unit, which generates a position or movement signal corresponding to a position or movement of the eye using the distance signal.

The method according to the invention can be carried out using the device according to the invention.

The invention takes advantage of the fact that the cornea of the eye has a typical shape, approximately that of a section of an ellipsoid or toroid surface, in particular of a calotte, and, thus, a measurement of the distance of the cornea from a reference plane, which is predetermined relative to the device according to the invention at least during operation and is essentially orthogonal to the detection ray bundle, allows the position or a change in the position of the cornea to be determined using the shape of the cornea.

According to the invention, said distance measurement is effected in a contactless manner, using optical radiation which, in connection with the invention, may also comprise, in particular, infrared radiation and/or visible light. In order to generate the optical radiation, the device according to the invention is provided with the illumination unit, which includes, in particular, a source of radiation for said optical radiation. Moreover, further deflecting or light-bundle forming elements may be provided in order to form the illumination ray bundle.

Infrared radiation is preferably used in order to avoid perception of the illumination ray bundle by the patient.

The illumination ray bundle is radiated onto the cornea of the eye where an illuminated spot or luminous spot forms. The cornea then returns the optical radiation of the illumination ray bundle as a detection ray bundle, preferably by reflection. Depending on the type of optical interaction (reflection, backscattering), the illumination ray bundle may be returned by different layers of the cornea, e.g. the epithelium, Bowman's membrane, Descement's membrane and/or the endothelium.

Using the optical radiation returned by the cornea as a detection ray bundle, distance signals are then generated, in a temporally resolved manner, which correspond to the distance of the cornea from the predetermined reference plane. For this purpose, the device according to the invention comprises the distance-determining unit, which receives at least part of the detection ray bundle and generates a distance signal from the properties of the detection ray bundle alone or in combination also with those of the illumination ray bundle. In so doing, the reference plane assumes a fixed position relative to the distance-determining unit and may, in particular, be given by the position of the distance-determining unit and/or the illuminating unit. The device preferably also comprises a head holder in which the head with the eye can be held in a predetermined position, such that movements of the eye due to the head moving can be largely excluded.

In particular, the distance-determining unit may comprise a photodetector for receiving at least part of the detection ray bundle, said photodetector being sensitive to at least one wavelength of the optical radiation used. The signals of the photodetector can be converted to the distance signals by a detection circuit in an analog and/or digital manner.

The time resolution, which is determined, among others, by the sensing frequency of the photodetector and the processing speed of the detection circuit, is preferably so large that even quick changes in the position or in the condition of movement of the eye can be precisely determined.

On the basis of said distance signals, position or movement signals corresponding to a position or movement of the eye are finally generated and output. For this purpose, the device according to the invention comprises an evaluating unit, which is connected to the distance-determining unit via a signal link in order to receive the distance signals and by means of which a position or movement signal corresponding to a position or movement of the eye can be generated using the distance signal. Whereas the position signal refers to the instantaneous position of the eye, a movement signal is understood to be a signal which expresses a change in position between at least two different sensing times or which, after division by a corresponding time interval, represents a corresponding speed.

A position or movement signal is thus formed on the basis of an assumption concerning the shape of the cornea in the region of the illumination beam or of a corresponding model. In particular, as mentioned above, it may be assumed, for measurement in the region of the vertex of the cornea, that the cornea, in this region, has approximately the shape of a region of an ellipsoid surface, in particular of a calotte, whose radius can be either assumed generally as a an average value or determined individually. In more precise models, different radiuses can be used for different layers. In this case, it is important to know by which of said layers the illumination ray bundle is returned the most.

The position or movement of the calotte or of the cornea and, thus, of the eye, can then be determined on the basis of the model of the cornea from the distance of the illuminated spot from the reference plane and the known direction of the illumination and detection ray bundles.

In doing so, the position or movement signal may be determined by analog or digital means. The operations to be carried out here are simple as compared to the above-described, video-based methods and can therefore be carried out very quickly by digital means, preferably by analog means.

The position or movement signal may then be output as digital or analog signals.

Therefore, the method and device according to the invention allow particularly simple and quick determination of the eye movement.

The possible spatial resolution capacity of the method or device according to the invention for the position of the eye depends, among others, on the ratio of the diameter of the region or spot on the cornea illuminated by the illumination beam to a radius of curvature of the cornea. Thus, it is preferred, in the method according to the invention, that the illumination ray bundle have a diameter of between 2 μm and 20 μm on the cornea. In the device according to the invention, the illuminating unit is preferably adapted such that, during operation, a diameter of the illumination ray bundle on the cornea of the eye arranged in front of the device is between 2 μm and 20 μm. With a diameter in this range, a better resolution is achieved than with illumination ray bundles having smaller diameters, wherein diffraction effects may deteriorate the spatial resolution, depending on the wavelength of use of the optical radiation. Particularly preferably, a diameter of 10 μm is used. In order to set the diameter of the ray bundle on the cornea, the illuminating unit may preferably comprise ray bundle forming optics. The ray bundle forming optics may comprise, in particular, at least one stop and one or more lenses.

The distance may be determined by different methods for optical determination of distances.

In a first alternative, use is made essentially of an interferometric method. Thus, it is preferred, in the method according to the invention, to couple out a reference ray bundle from the illumination ray bundle, said reference ray bundle having the detection ray bundle superimposed thereon, and to generate the distance signal by detecting interferences of the superimposed ray bundles. In the device according to the invention, it is preferred, for this purpose, that the distance-determining unit comprise an interferometer portion, by which an interferometer is formed together with the cornea during operation. In this case, the cornea acts as an element which returns optical radiation. Thus, a reference ray bundle is coupled out from the illumination ray bundle, said reference ray bundle having superimposed thereon the illumination ray bundle, returned by the cornea as a detection ray bundle. While the reference ray bundle travels a known optical path, which is constant over time or variable, the optical path length traveled by the illumination ray bundle after coupling out and after reflection by the cornea as a deflection ray bundle depends on the position of the cornea. Interferences which can be detected by means of a detection unit of the distance-determining unit occur if the resulting optical path difference is smaller than the temporal coherence length of the optical radiation of the illumination beam. Such method enables a simple optical structure.

Particularly preferably, the method and device according to the invention may be provided in a manner similar to an optical coherence tomograph. In the method according to the invention, it is preferred to vary the optical path length for the reference ray bundle before superposition, the illumination beam after splitting off the reference ray bundle and/or the detection ray bundle before superposition, according to a predetermined time program, to detect the intensity of the superimposed reference and detection ray bundles in a temporally resolved manner according to the time program, and to generate a distance signal on the basis of the detected intensity. For this purpose, it is preferred, in the device according to the invention, that the illumination unit be provided to emit optical radiation having a predetermined temporal coherence length, the interferometer portion comprise at least one beam splitter arranged in the path of the illumination ray bundle so as to generate a reference ray bundle from the optical radiation of the illuminating unit, at least one optical functional element for superimposing the detection ray bundle on the reference ray bundle, and a unit for varying the optical path length of the path of the reference ray bundle between the beam splitter and the optical functional element or the optical path length of the path of the illumination ray bundle after the beam splitter and/or between the spot illuminated by the illumination ray bundle on the cornea and the optical functional element, according to a predetermined time program, and the distance-determining unit comprise a detection unit by means of which the intensity of the superimposed reference and detection ray bundles can be sensed according to the time program and converted to a distance signal. In particular, the distance of the cornea can be measured by determining at which optical path length difference an interference occurs. This is because, for interference to occur, it is required that the amount of the path length difference be smaller than the temporal coherence length. In this embodiment, a simple device may be used which can sense a large distance range with high precision. In particular, the optical functional element may also be part of the unit for varying the optical path length.

In order to obtain a particularly good resolution of the distance determination, it is preferred that the temporal coherence length of the optical radiation of use be between 1 μm and 10 μm.

In principle, the variation of the optical path difference may be effected in any desired manner. For example, a change in refractive index along at least part of the path is possible. However, in the method it is preferred to move a reflector back and forth linearly in order to vary the optical path length. For this purpose, it is preferred, in the device according to the invention, that the unit for varying the optical path length comprise a reflector which is movable back and forth in a linear manner. In this way, the optical path length is particularly easy to change even over larger ranges, while the position of the reflector is easy to determine at the same time. In order to move the reflector, a corresponding drive unit may be provided, in particular, by means of which position signals can be emitted, which indicate the position and, thus, the length of the optical path of the reference ray bundle.

In another variant of the method, it is preferred to rotate a plurality of reflecting surface portions about an axis in order to vary the optical path length, said portions having different radial spacing from said axis. For this purpose, it is preferred, in the device according to the invention, that the unit for varying the optical path length comprise a reflector assembly which is rotatable or pivotable about an axis by a drive, said assembly comprising a plurality of reflecting portions, each differently spaced from the axis. Particularly preferably, the rotation is effected at a constant frequency of rotation either continuously or step by step. The axis of rotation may be oriented, in particular, orthogonal to the direction of the reference ray bundle. In such an arrangement, the optical path length may be changed at a constant speed during a rotation of the mirror. Moreover, the mechanical demands placed on the bearing of the reflector assembly are not very high, because out-of-balance errors can be avoided by suitable mass distribution in the reflector assembly. If an assembly comprising a plurality of plane reflector surfaces is used, the distances of adjacent reflector surfaces preferably differ by one to two temporal coherence lengths. In this manner, a particularly good distance resolution is obtained.

In a second alternative for determining the distance, it is preferred, in the method according to the invention, that the illumination ray bundle be focused for at least one wavelength in a predetermined range of possible positions of the cornea, that the detection ray bundle be focused in the region of a small-aperture stop by means of detection optics, the aperture of said stop being located, for said wavelength, in a plane which is conjugated, with respect to the detection optics, with an object plane associated with the wavelength and lying in the predetermined range of possible positions of the cornea and that the distance signal be generated by detection of the optical radiation passing through the small-aperture stop. In the device according to the invention, it is preferred, for this purpose, that the device comprise illumination optics for focusing the illumination ray bundle for at least one wavelength in a predetermined range of possible positions of the cornea, and that the distance-determining unit comprise detection optics in a detection beam path, a small-aperture stop arranged following said detection optics and a detection unit arranged following the small-aperture stop in order to detect the optical radiation behind the small-aperture stop, with a plane of an aperture of the small-aperture stop being conjugated, with respect to the detection optics for the wavelength, to an object plane associated with said wavelength in the range of possible positions of the cornea with respect to the detection optics. A small-aperture stop is understood herein to be an small-aperture stop having a very small aperture, which is often referred to also as a "pinhole" or a "pinhole stop". By means of the illuminating unit, the optical radiation for at least one wavelength is focused in the predetermined range of possible positions of the cornea, said optical radiation illuminating the cornea. The range of possible positions of the cornea is predetermined and fixed with respect to the distance-determining unit. In particular, it is determined by the imaging geometry of the illumination optics. In the use of the invention, the eye of the patient is to be brought into this range by suitably positioning the patient. A substantial portion of the optical radiation returned by the cornea will only pass through the small-aperture stop and reach the detection unit if the real or virtual focus of the illumination ray bundle returned by the cornea is located in the object plane associated with the wavelength and set by the device or in a region around said object plane having a width which corresponds to the depth of focus of the detection optics. In particular, the focus may be located on the surface of the cornea. This focus is then imaged into the aperture of the small-aperture stop and can pass through it. The distance of the cornea from the reference plane can be determined from the position of the object plane relative to the reference plane, when optical radiation passes through the small-aperture stop. In this respect, the, per se known, method of confocal detection of reflected light at surfaces is used. This embodiment allows the use of illumination units independent of the coherence characteristics of the emitted optical radiation achievable thereby.

In an embodiment of the method according to the invention, it is then preferred that the range of possible distances of the cornea from the reference plane be scanned by changing the distance between the object plane and the small-aperture stop. In this way, on the one hand, a predetermined distance range can be scanned by movement of the object plane associated with the wavelength. This may be effected, in particular, by moving the illumination and/or detection optics and/or by changing the focal length of the illumination and/or detection optics. A change in the focal lengths may be enabled, for example, by using a motor-adjustable zoom lens. On the other hand, it is possible to move the small-aperture stop in the direction of the detection beam path in order to scan the distance range. Finally, a combination of these methods is also possible. It is therefore preferred, in the device according to the invention, that the position of the illumination and/or detection optics and/or of the small-aperture stop and/or the focal length of the illumination and/or detection optics be variable within a predetermined range by means of a drive. A significant part of the detection ray bundle will pass through the small-aperture stop if the real or virtual focus of the illumination ray bundle returned by the cornea is located in the object plane conjugated with the plane of the aperture of the small-aperture stop. Correlation of the detection of a corresponding intensity with the corresponding position or focal length of the respective optical element then allows to generate the distance signal. This embodiment allows the use of simple optical elements, in particular if the optical radiation of the illumination ray bundle is very narrow-band.

In order to enable particularly quick distance determination, it is particularly preferred, in the method according to the invention, to use optical radiation of different wavelengths and to guide the illumination and/or detection ray bundle through at least one optical functional element exhibiting a strong chromatic longitudinal aberration. In this case, "strong" means that the longitudinal aberration exceeds the Rayleigh length. It may be, for example, a strongly dispersive element. Therefore, for simplification, a strongly dispersive element is also referred to in the following.

A distance signal can be generated by determining the wavelength of the optical radiation behind the small-aperture stop. In the device according to the invention, it is preferred, for this purpose, that optical radiation of different wavelengths can be emitted by means of the illuminating unit and that ray bundle forming optics of the illumination unit, the illumination optics, and/or the detection optics have a strong longitudinal aberration. In this manner, spaced apart object planes, conjugated with the small-aperture stop, are simultaneously formed for different wavelengths, so that a corresponding distance range can be simultaneously scanned.

If the ray bundle forming optics and/or the illumination optics are strongly dispersive, those parts of the illumination ray bundle, possibly reflected by the cornea, which have different wavelengths, are focused on spaced apart planes in the region of the cornea, which are associated with the respective wavelengths. Only such parts reflected by the cornea will pass the small-aperture stop with significant intensity, whose focus is located in the object plane corresponding to the wavelength.

In case of the detection optics having a strong longitudinal aberration, the parts of the detection ray bundle are focused at different distances from the small-aperture stop according to their wavelengths, so that only those parts of the illumination ray bundle returned by the cornea pass through the small-aperture stop, which are imaged into the small-aperture stop. These are portions whose focus is located in the associated object plane after or during reflection by the cornea. A specific distance of the cornea from the device then corresponds to said wavelength. In this way, the use of moving parts, such as rotating or oscillating mirrors, for example, can be avoided.

In order to achieve good resolution with, at the same time, low demands on the intensity radiated onto the eye, it is preferred that the illumination ray bundle in the object plane associated to the wavelength have substantially the same diameter as the small-aperture stop. In this case, the ray bundle diameter is preferably in the range of between 2 µm and 20 µm. What is particularly preferred is a ray bundle diameter of about 10 µm.

Optical radiation having different wavelengths can be provided in different ways. For instance, according to one embodiment of the method of the invention, it is preferred that illumination ray bundles of optical radiation in at least two different spectral ranges be alternately used in a predetermined time sequence. It is thus preferred, in the device according to the invention, that the illuminating unit be provided for emission of optical radiation in at least two different spectral ranges in a predetermined time sequence. The change in wavelengths may preferably be effected at a frequency which is so high that even a rapid eye movement can still be tracked, e.g. at frequencies of more than 100 Hz, preferably more than 10 kHz. For this purpose, the illuminating unit may comprise at least two source of radiation emitting optical radiation of respectively different wavelengths and/or different colors. For example, suitably controlled light-emitting diodes or lasers may be used. This will keep the power output of the optical radiation on the eye very low. Moreover, sources of radiation of respectively low mean power can be used.

In another embodiment of the method according to the invention, it is preferred that the illumination ray bundle comprise optical radiation in one spectral range. It is thus preferred, in the device according to the invention, that the illuminating unit comprise a source of radiation for emission of optical radiation in a predetermined spectral range. For this purpose, the spectral range is selected in relation to position and width preferably as a function of the chromatic longitudinal aberration of the dispersive functional element or of the illumination and/or detection optics, respectively. The width is preferably in the range of about $\Delta\lambda > \lambda/5$. In particular, the spectral range may be between 400 nm and 700 nm. Thus, a continuum of focus positions may be obtained, which allows precise distance determination. Illumination units for emission of optical radiation in a spectral range are very easy to produce, because they may comprise, for example, a light bulb or a white light-emitting diode as sources of radiation. The latter is characterized, among others, by a very minor heat development and a very low emission of heat radiation occurring outside the desired spectral range. Further, a superluminescence diode may be used whose emission spectrum comprises a spectral band in the red region between 635 nm and 670 nm having a width of between 20 nm and 50 nm.

From that part of the detection radiation which passes through the aperture stop, the distance can be deducted or a distance signal can be generated in different ways. According to one embodiment of the method of the invention, it is preferred to detect the intensity of the detection ray bundle behind the small-aperture stop in a spectrally and temporally resolved manner while generating the distance signal. For this purpose, it is preferred, in the device according to the invention, that the detection unit be adapted for spectrally resolved and temporally resolved detection of the optical radiation following the small-aperture stop. To this end, the detection unit may comprise, in particular, a spectrometer. Particularly preferably, however, a color-sensitive photodetector is used. This embodiment is characterized by a particularly simple and robust structure. The distance of the cornea from the device can then be deduced from the color of the received optical radiation. This type of detection is suitable for the two above-described alternatives of illumination, wherein the frequency at which the optical radiation is detected should be so low, in the case of the first alternative, that all colors used should be emitted the same number of times during one cycle of detection. Since all wavelengths in the range of sensitivity of the photodetector are simultaneously detectable, the eye movement can be tracked very quickly, in particular in connection with the second above-mentioned method of illumination.

In another embodiment of the method according to the invention, wherein optical radiation with wavelengths changing over time is used for illumination, it is preferred that, timed according to the change of the spectral ranges of the illumination ray bundles, the intensity of the detection ray bundle after pinhole is detected while generating the distance signal. In this respect, it is preferred, in the device according to the invention, that the detection unit be adapted for temporally resolved detection of the optical radiation following the small-aperture stop. The detection unit of this embodiment may comprise a simple photodetector which merely needs to be sensitive at the wavelengths of use. However, spectral resolution is not required. To allow detection of the radiation passing through the small-aperture stop synchronously with the change in wavelengths of the optical radiation, it is possible to couple, in particular, a corresponding detection circuit for evaluating the signals of the photodetector, with a circuit of the illumination unit for controlling the change in spectral ranges of the optical radiation.

In order to enable the use of a compact device for determining the eye movement, it is preferred, in the method according to the invention, that the illumination ray bundle be irradiated onto the cornea at an angle of incidence of less than 10°, preferably less than 5°. In this case, the angle of incidence is understood to be the angle between the illumination beam and a normal on a tangential surface at the region of the cornea illuminated by the illumination ray bundle. A particularly favorable solution is obtained if the illumination radiation has a high numerical aperture, so that the angle of incidence is considerably smaller than the angle of convergence of the illumination radiation, the latter angle being obtained from the numerical aperture. Particularly preferably, the radiation direction is substantially orthogonal to the cornea in at least a central position of the eye. Moreover, this arrangement also allows particularly easy determination of the distance due to the simple beam path.

This arrangement makes particularly efficient use of the illumination radiation employed, because a maximum amount of the radiation returned by the cornea can be received by the detection optics.

In the device according to the invention, it is thus preferred, that the illumination optics and the detection optics comprise a common objective. A semi-transparent reflector may be arranged in the illumination beam path, said reflector deflecting the detection ray bundle out of the illumination beam path. As an alternative, a semi-transparent reflector may be arranged in the detection beam path, said reflector coupling the illumination ray bundle into the detection beam path—counter to the direction of the detection ray bundle. The device is thus merely required to comprise a corresponding objective which substantially simplifies its structure. Moreover, otherwise required, complex adjustments may be dispensed with.

It is particularly preferred that the common objective have a strong longitudinal aberration. In this way, a chromatic aberration is caused during focusing of both the illumination ray bundle and the detection ray bundle, which leads to a particularly great total aberration. Said total aberration in turn enables a better resolution capacity for determination of the distance.

Basically, the method according to the invention can be used in order to determine the movement of the eye in only one direction. However, it is preferred to illuminate at least two different regions on the cornea with at least two different illumination ray bundles, to generate, in a temporally resolved manner, distance signals relating to the distances of the cornea from respectively corresponding, predetermined reference planes, using the optical radiation respectively returned by the cornea as detection ray bundles, and to generate position or movement signals relating to a position or movement of the eye in at least two spatial directions on the basis of the distance signals. For this purpose, it is preferred, in the device according to the invention, that one or more illumination units be adapted for forming two illumination ray bundles of optical radiation for illumination of two different regions on the cornea of the eye, that detection ray bundles of optical radiation returned by said two regions on the cornea be receivable in a temporally resolved manner and that it be possible to generate distance signals using the received optical radiation of the detection ray bundle, said signals corresponding to distances of the cornea from two reference planes, which are respectively defined for one said detection ray bundle relative to the distance-determining unit, and that the evaluating unit be adapted for generating position or movement signals corresponding to a position or movement of the eye in two spatial directions using the distance signals. Since the cornea is approximately rotation-symmetrical to the optical axis of the eye, the movement in only one spatial direction can thus also be determined more precisely, because a movement in two spatial directions could lead to errors in an evaluation assuming a movement in only one spatial direction. In this case, the different above-described embodiments of the method or device according to the invention can be respectively used for each of the illumination ray bundles and the respective detection ray bundles at least in an analogous manner. If only one illuminating unit is used, it may either comprise two separate sources of radiation or only one source of radiation and a beam splitter by which two separate illumination ray bundles can be formed. In this case, the distance may be respectively determined by the above-described preferred embodiments and improvements of the method according to the invention. Accordingly, the illumination unit(s) and the distance-determining unit(s) may be provided in accordance with the above-described preferred embodiments and improvements of the device according to the invention. A different method may be used for each illumination ray bundle.

In order to obtain full information on the movement of the eye, it is preferred to illuminate at least three different regions on the cornea with at least three different illumination ray bundles, said regions forming corners of a triangle, to generate, in a temporally resolved manner, distance signals relating to the distances of the cornea from respective corresponding reference planes, using the optical radiation returned by the cornea as respective detection ray bundles, and to generate position or movement signals relating to a position or movement of the eye in three spatial directions, on the basis of the distance signals. It is preferred, in the device according to the invention, that one or more illumination units be provided for forming three illumination ray bundles of optical radiation for illumination of three different regions on the cornea of the eye, said regions forming corners of a triangle, that detection ray bundles of optical radiation returned by said three regions on the cornea be receivable in a temporally resolved manner and that it be possible to generate distance signals using the received optical radiation of the detection ray bundles, said signals corresponding to distances of the cornea from three reference planes, which are respectively defined for one said detection ray bundle relative to the distance-determining unit, and that the evaluating unit be provided for generating position or movement signals corresponding to a position or movement of the eye in three spatial directions using the distance signals. In this way, the position of the cornea can be easily and quickly determined in three dimensions. If only one illuminating unit is used, it may either comprise two separate sources of radiation or only one source of radiation and a beam splitter by which three separate illumination ray bundles can be formed. In this case, the distance may be respectively determined by the above-described preferred embodiments and improvements of the method according to the invention. Accordingly, the illumination unit(s) and the distance-determining unit(s) may be provided in accordance with the above-described preferred embodiments and improvements of the device according to the invention. A different method may be used for each illumination ray bundle.

BRIEF DESCRIPTION OF THE DRAWINGS

The invention will be explained in more detail below, by way of example and with reference to the drawings, wherein.

DETAILED DESCRIPTION OF THE INVENTION

Figure 1:
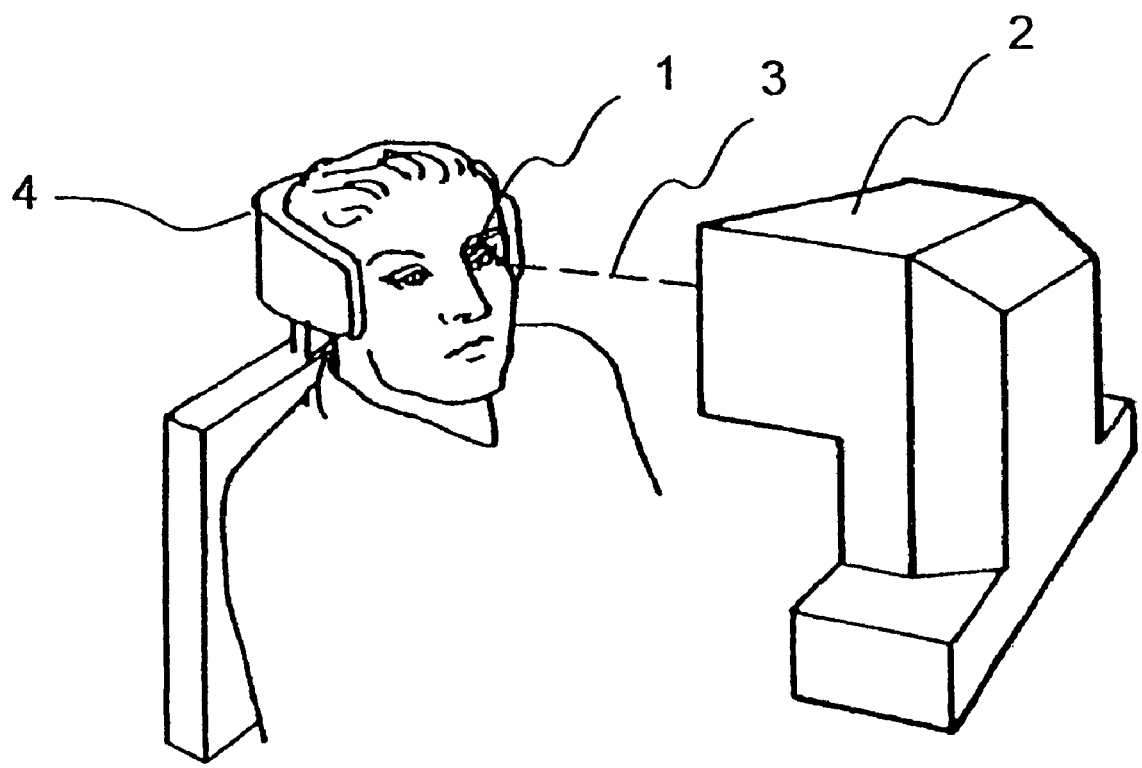
FIG. 1 shows a schematic perspective view of a patient during a laser surgery treatment using a laser surgery instrument which comprises a movement-determining device according to a first preferred embodiment of the invention.

In FIG. 1, the eye 1 of a patient is being treated by means of a treatment laser beam 3 emitted by a laser surgery instrument 2. For this purpose, the patient's head is held in a head holder 4, which assumes a position that is initially adjustable, but remains fixed during operation, relative to the laser surgery instrument 2, with which the head holder 4 may be connected, in particular.

Figure 2:
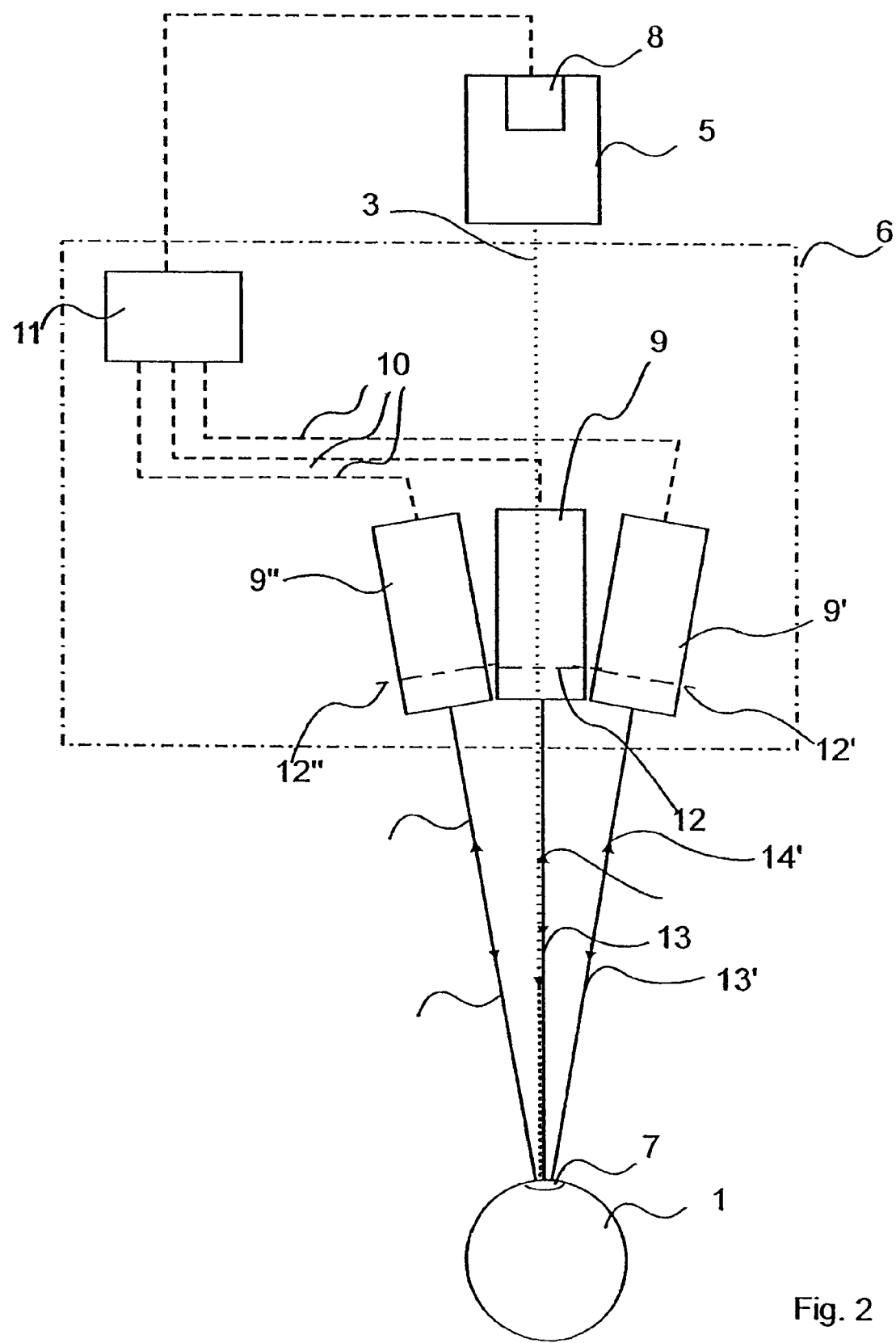
FIG. 2 shows a schematic view of the laser surgery instrument in FIG. 1, together with an eye.

The laser surgery instrument 2 is shown in more detail in a schematic view in FIG. 2. Said instrument comprises, on the one hand, the actual treatment unit 5 and, on the other hand, a movement-determining device 6 for determining a movement of the eye 1 during treatment and outputting corresponding movement or position signals. Further, a fixing light source, not shown in the Figures, may be provided onto which the patient can fix his gaze during treatment and thus suppress any voluntary movements of the eye.

The treatment unit 5 comprises a treatment laser, not specifically shown in the Figures, said laser comprising treatment optics for focusing and moving the treatment laser beam 3 onto the cornea 7 of the eye 1. The treatment optics are adjustable by a control unit 8, which is shown only very schematically, for moving the treatment laser beam 3.

The control unit 8 moves the treatment laser beam 3, on the one hand, as a function of a path given by the treatment in the case of the cornea 7 not moving and, on the other hand, as a function of an involuntary movement of the eye 1, which movement is detected by the movement-determining device 6. By moving the treatment laser beam 3 accordingly, the control unit 8 thus compensates for a change in the relative position between the treatment laser beam 3 and the eye 1 or the cornea 7, said change being caused by voluntary and/or involuntary eye movements, e.g. saccades, microsaccades, torsional movements, etc. For this purpose, the control unit 8 is connected to outputs of the movement-determining device 6, via which it receives the movement or position signals from the movement-determining device 6.

The movement-determining device 6 comprises three equally designed sensing units 9, 9', 9'', which are connected to an evaluating unit 11 via signal links 10.

The sensing units 9, 9', 9'' respectively sense a distance of the cornea 7 from reference planes 12, 12' and 12'', which are each associated with a respective sensing unit in a spatially fixed manner. For this purpose, optical radiation from each of the sensing units is irradiated as a respective illumination ray bundle 13, 13', 13'' onto the cornea 7, and the optical radiation returned by the cornea 7 is received as a respective detection ray bundle 14, 14', 14'', which is orthogonal to the respective reference plane. Apart from the orthogonal orientation to the respective detection ray bundle, the position of the reference planes 12, 12' and 12'' can be arbitrarily predetermined, but it is fixed relative to the respective sensing unit. Using the detection ray bundles 14, 14' and 14'', respectively, one distance signal each is then generated in a temporally resolved manner, which signal represents the distance of the cornea 7 from the respective reference plane.

Figure 3:
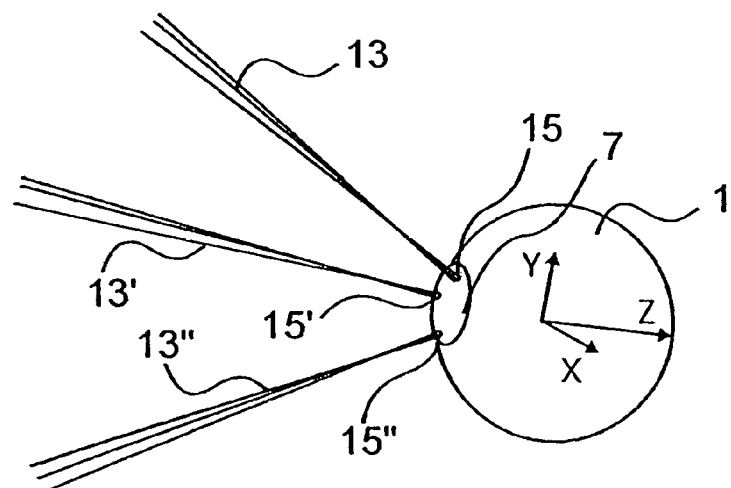
FIG. 3 shows a schematic view of the eye in FIG. 2 and of three illumination and detection ray bundles of the movement-determining device of FIG. 2.

The sensing units 9, 9' and 9'' can be positioned relative to each other (cf. FIG. 3) so that the illumination ray bundles 13, 13' and 13'', respectively, illuminate spots 15, 15', 15'' on the cornea 7, which are located approximately on the corners of a triangle or spherical wedge. These spots are preferably located on the edge of the cornea or in regions where their topography deviates the most from a spherical shape. The illumination ray bundles 13, 13' and 13'', respectively, are incident on the cornea 7 at an angle of incidence which is less than approximately 10° to a normal on the cornea 7.

The evaluating unit 11 receives the distance signals of the three sensing units 9, 9', 9'', from which it determines movement and position signals, which are output to the treatment unit 5.

In order to generate the movement or position signals, the cornea 7 is assumed to have the shape of a calotte with a known radius in that portion which can be reached by the illumination ray bundles. More precise measurements are possible if the shape of the cornea was previously measured by a topography instrument and these data are available to the evaluating unit 11.

Depending on the required precision, an average corneal curvature of the human eye may be assumed, or the corneal curvature may be determined individually for a patient. For this purpose, either a separate determination may be effected before treatment is started, or the corneal curvature may be determined in the course of the determination of movement by analysis of the distance data, if a purely coincidental movement of the eye 1 may be assumed with the same likelihood in all directions.

The structure and function of the sensing units 9, 9' and 9" will now be explained in more detail taking the sensing unit 9 as an example.

An illumination unit 16 irradiates optical radiation as an illumination ray bundle 13 onto a distance-determining unit 17 comprising a portion 18 of an interferometer, which forms a Michelson interferometer together with the cornea 7, and a detection unit, which comprises a photodetector 19 with a subsequently arranged detection circuit 20 (cf. FIG. 4).

The illumination unit 16 comprises a laser for generating an illumination ray bundle 13 with optical radiation of a predetermined coherence length of approximately 5 μm in a narrow wavelength region around e.g. 780 nm and, arranged following the laser in the beam path, a ray bundle forming unit, which is not shown in detail in the Figures, and by which the illumination ray bundle 13 may be transformed into a substantially parallel ray bundle.

The illumination units of the three sensing units 9, 9' and 9" form an illumination unit in the sense of the invention.

The interferometer portion 18 comprises a beam splitter 21, which is arranged in the beam path of the illumination ray bundle 13 at an angle of 45°. One part of the illumination ray bundle 13 is deflected as a reference ray bundle 22 into a reference arm 23 of the interferometer portion 18, while the other part passes through the beam splitter 21 and is coupled into a measuring arm 24.

The reference arm 23 comprises a reflector 25, oriented orthogonal to the direction of the reference ray bundle 22, said reflector 25 being movable back and forth in the direction of the reference ray bundle 22 between predetermined positions according to a predetermined time program by means of a reflector drive 26, which is shown only schematically. The reflector drive 26 is connected to the detection circuit 20 via a connecting line through which it transmits position signals in respect of the position of the reflector to the detection circuit 20. The optical path length for the reference ray bundle 22 in the reference arm 23 from the beam splitter 21 via the reflector 25 and back to the beam splitter 21 is, therefore, variable in time according to the time program.

Figure 4:
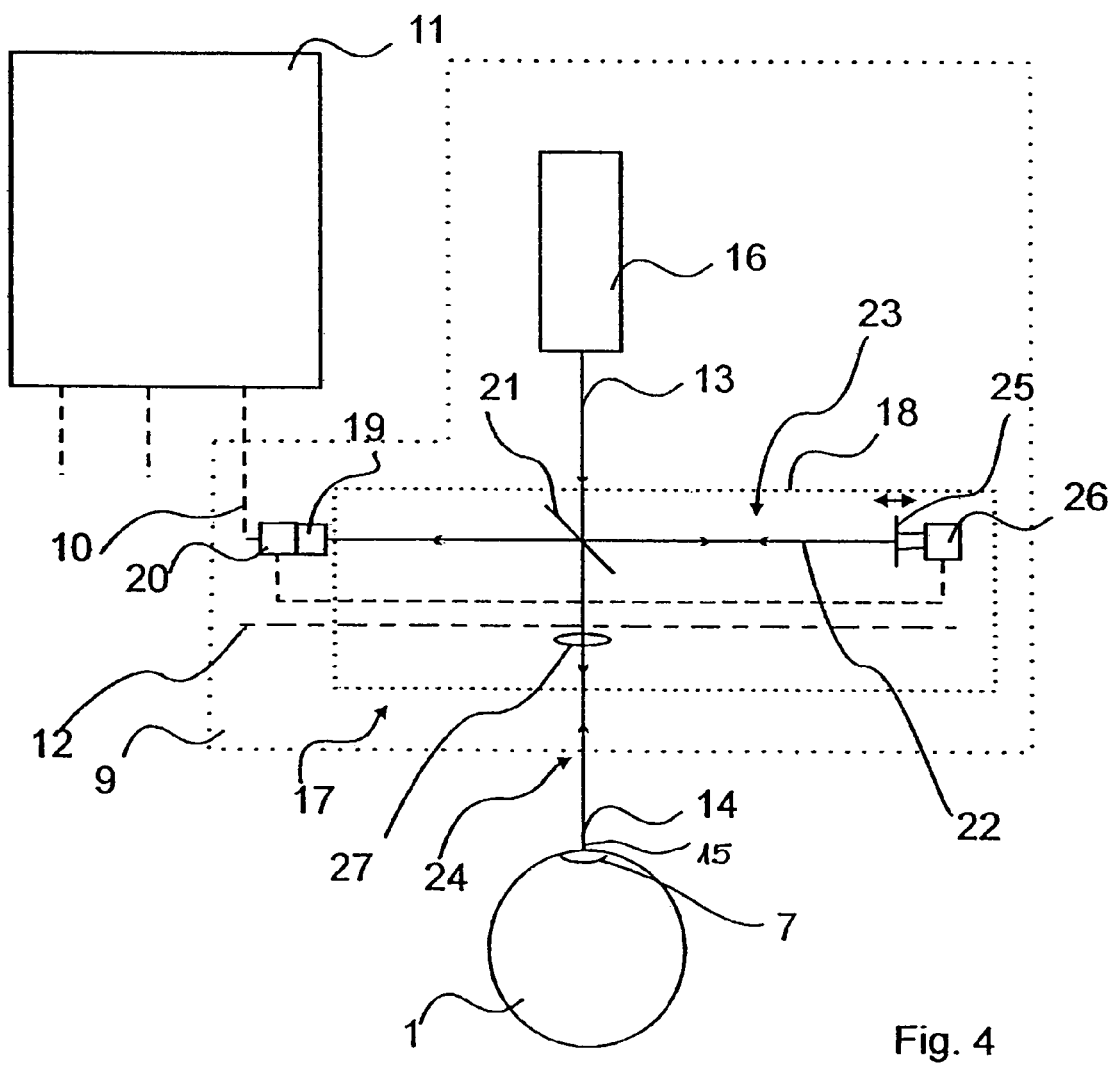
FIG. 4 shows a schematic view of an eye and of part of the movement-determining device of FIG. 2, comprising a sensing unit for a direction of eye movement and an evaluating unit.

In the measuring arm 24, illumination optics 27, shown only very schematically in FIG. 4, are arranged following the beam splitter 21 in the beam path of the illumination ray bundle 13, said illumination optics focusing the illumination ray bundle 13 in the area of the cornea 7 of the eye 1. The illumination optics 27 are provided such that the focus has an extension, in the direction of the illumination ray bundle 13, which corresponds approximately to the changes in distance to be expected between the cornea 7 and the reference plane 12. The illumination ray bundle 13 generates an illuminated spot 15 having a diameter of approximately 10 μm on the cornea 7 (cf. FIG. 3).

The optical radiation of the illumination ray bundle 13 returned by the cornea 7 as detection ray bundle 14 is returned to the beam splitter 21 by the illumination optics 27, which thus simultaneously function as detection optics, said beam splitter 21 deflecting part of the detection ray bundle 14 onto the photodetector 19.

The part of the detection ray bundle 14 deflected by the beam splitter 21 therefore has superimposed thereon the reference ray bundle 22 which passes through the beam splitter 21.

Figure 5:
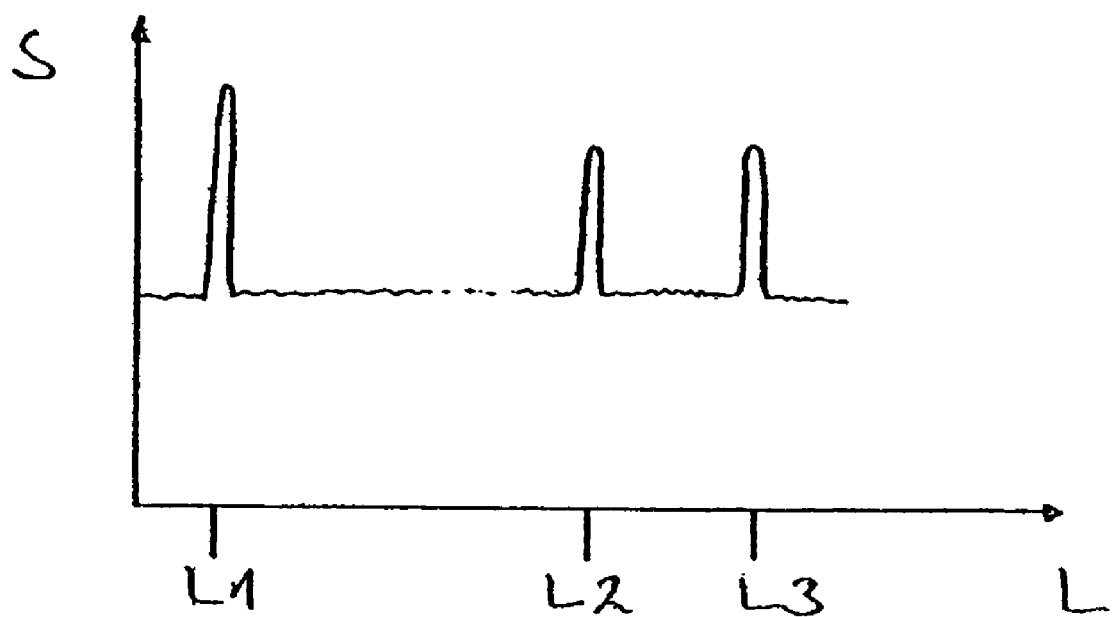
FIG. 5 shows a schematic view of a signal profile of a photo detector of the sensing unit in FIG. 4 during operation.

Depending on the optical path length of the reference arm 23 and the measuring arm 24, interferences may occur between these beams, which interferences can be sensed by the photodetector 19. FIG. 5 shows a typical signal profile as a function of the path length L of the reflector 25. At first, no interferences occur, because the difference between the optical path lengths is greater than the temporal coherence length of the illumination ray bundle 13. If the amount of the difference is less than the coherence length, however, interference does occur. Since a plurality of jumps in refractive index occur in the cornea 7 of the eye, at each of which jumps a reflection takes place, there is a plurality of measuring arms, in a way, of correspondingly different optical path lengths. At first, an interference caused by the reflection at the cornea occurs at position L1, then further interferences at positions L2 and L3 occur by reflection at the subsequent jumps in refractive index, e.g. between the stroma and Bowman's membrane.

The photodetector 19 receives the superimposed ray bundles. The detection circuit 20 senses corresponding intensity signals and position signals of the reflector drive 26 with respect to the reflector 25 at a predetermined frequency (e.g. 400 kHz), which is higher than the frequency at which the reflector 25 is reciprocated. In so doing, the detection circuit 20 only senses the occurrence of the first interference and the corresponding position L1, which allows to determine the optical path length of the reference arm 23 and thus—up to the coherence length—the optical path length of the measuring arm 24. The detection circuit then outputs a distance signal corresponding to the position L1, which is a measure for the distance of the cornea 7 from the beam splitter 21 or the reference plane 12. In this case, the inaccuracy of the distance is given by the temporal coherence length of the optical radiation.

In order to obtain a minimal temporal coherence length and, thus, a high distance resolution, use is preferably made of lasers or super-luminescence diodes having a broad emission spectrum, because the temporal coherence length (i.e. the coherence length in the beam direction) decreases as the emission bandwidth increases.

In a further, second embodiment a reflector arrangement, which is rotatable about an axis of rotation orthogonal to the reference ray bundle 22, is used instead of the linearly moved reflector 25. The reflector arrangement comprises reflector surfaces, which are arranged at equal angular intervals relative to each other about the axis of rotation, said surfaces being arranged at distances from the axis of rotation which increase in equal steps. Rotation of the reflector arrangement then allows the optical path length of the reference arm to be changed, in which case, instead of the position signals, corresponding angular position signals are output to the detection circuit.

A movement-determining device according to a third embodiment differs from the movement-determining device of FIG. 2 in the design of the sensing units. Otherwise, it is identical in structure and is connected to the treatment unit 5. Further, illumination units of the sensing units also provide illumination devices of the movement-determining device in this case. Therefore, the same reference numerals are used for identical or analogous components, and the corresponding statements also apply here.

Figure 6:
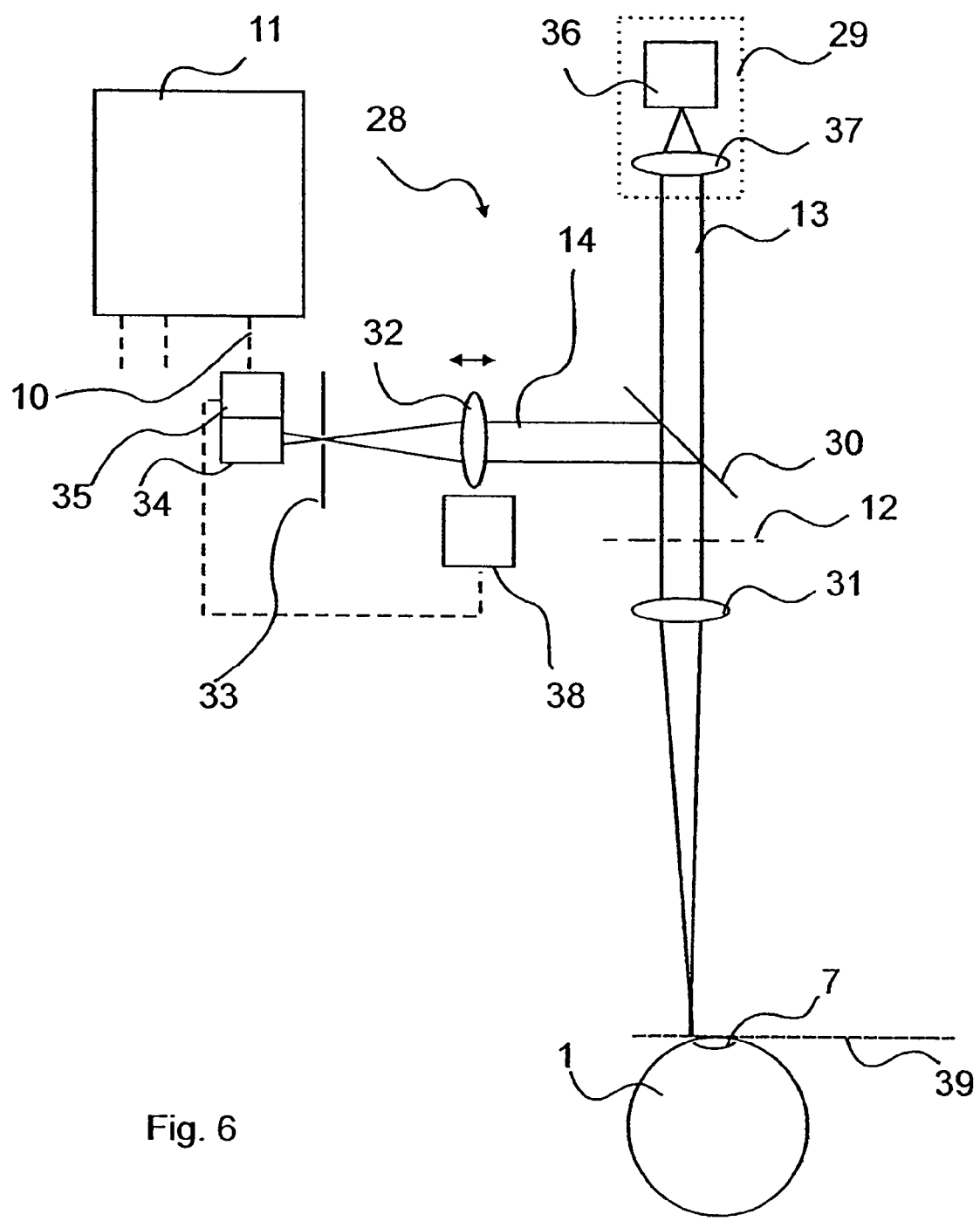
FIG. 6 shows a schematic view of an eye and of part of a movement-determining device according to a third embodiment.

The sensing unit 28 shown in FIG. 6 does not use an interferometer, but instead uses a structure for determining distances by means of confocal imaging.

An illumination unit 29 generates an illumination ray bundle 13 for illuminating the cornea 7. In the linear beam path of the illumination ray bundle 13 there are arranged, at an angle of 45° to the illumination ray bundle 13, a semi-transparent mirror 30 and illumination optics 31, shown only schematically, which comprise an objective, so that the illumination ray bundle 13 passes through the semi-transparent mirror 30 and is focused by the illumination optics 31 in a predetermined range of possible positions of the cornea 7. Said range is determined by the position of the sensing unit 28 and the imaging geometry of the illumination optics 31, so that the cornea 7 has to be put in said range by positioning the patient accordingly.

The optical radiation of the illumination ray bundle 13 is returned by the cornea 7 as a detection ray bundle 14.

In the beam path of the detection ray bundle 14, there are arranged the illumination optics 31, the semi-transmitting mirror 30, which deflects the detection ray bundle 14, focusing optics 32 which are shown only schematically, and a small-aperture stop 33 arranged following said focusing optics 32 and having an aperture diameter of approximately 10 μm. The small-aperture stop is also referred to as a "pinhole" stop. Therefore, the illumination optics 31 and the focusing optics 32 form detection optics.

Arranged following the aperture stop 33 is a photodetector 34, which is connected to a detection circuit 35.

The illumination unit 29 comprises a narrow-band light-emitting diode 36 or a laser as the source of radiation as well as, arranged following it, ray bundle forming optics 37, only schematically shown, in which the divergence of the optical radiation emitted by the light-emitting diode 36 is reduced by means of two lenses or lens systems and a stop arranged between them.

The position of the focusing optics 32 along the direction of the detection ray bundle 14 is adjustable by a drive 38 according to a predetermined time program. As an alternative, the optics 31 may be adjusted as well, thus keeping the focal plane of the LED and of the pinhole 33 conjugated with each other, which leads to marked peaks and, thus, to better signals. For transmission of position signals indicating the position of the focusing optics 32, the drive 38 is connected to the detection circuit 35. The range of possible positions is selected so that an object plane 39 in the predetermined range of possible positions of the cornea 7 can be conjugated with a plane passing through an aperture of the aperture stop 33, by changing the position of the focusing optics 32 and thus the position or focal length of the detection optics.

Thus, the semi-transmitting mirror 30, the illumination optics 31, the focusing optics 32, the drive 38, the small-aperture stop 33, the photodetector 34 and the detection circuit 35 form a distance-determining unit.

The parallel illumination ray bundle 13 emitted by the illumination unit 29 is focused by the illumination optics 31 in the region of the cornea 7. Thereby, the illumination ray bundle 13 generates an illuminated spot 15 on the cornea 7 and is reflected at least in part. The detection ray bundle 14 thus produced is focused in the region of the aperture stop 33 by means of the illumination optics 31, the semi-transmitting mirror 30 and the focusing optics 32. Therefore, a significant part of the detection ray bundle 14 can only pass through the aperture stop 33 if the real or, depending on the position of the cornea 7, the virtual focus of the illumination ray bundle 13 reflected by the cornea 7 is located in the object plane 39 which is conjugated with the aperture stop 33. Otherwise, only a small part of the detection ray bundle 14 reaches the photodetector 34. If said part does not exceed a predetermined threshold value, the detection circuit 35 will detect no detection ray bundle 14.

In order to allow the position of the cornea 7 to be determined in movement, the object plane 39 is displaced by adjusting the position of the focusing optics 32, and thus the position and focal length of the detection optics, according to the predetermined time program.

The detection circuit 35 works in cycles having a predetermined cycle frequency, which is so great that a movement of the eye is tracked with a desired temporal and spatial resolution. In each cycle, upon recognition of a detection ray bundle 14 on the photodetector, the detection circuit 35 determines the position of the object plane 39 and thus the distance of the cornea 7 from the reference plane 12 on the basis of the position signal from the drive 38 and outputs a corresponding distance signal.

An advantageous embodiment is obtained if the optics of use are color-corrected. This allows the use of broadband light sources. As an alternative, instead of the position of the object plane 39, the position of the aperture stop 33 may also be varied, while the position of the focusing optics 32 remains fixed.

A movement-determining device according to a fourth embodiment, which enables a better S/N ratio, differs from the movement-determining device of the third embodiment by the sensing units 40. Otherwise, it is identical in structure and is connected to the treatment unit 5. Therefore, the same reference numerals are used for identical or analogous components, and the corresponding statements also apply here. In this case, too, illumination units of the sensing units are simultaneously also illumination units of the movement-determining device.

This embodiment dispenses with an adjustable position of the focusing optics 32. Instead of the positionally adjustable, color-corrected focusing optics 32, strongly dispersive focusing optics 41 are used. Furthermore, instead of the illumination unit 29, an illumination unit 42 is used, and instead of the photodetector 34, a photodetector 43 is used.

Figure 8:
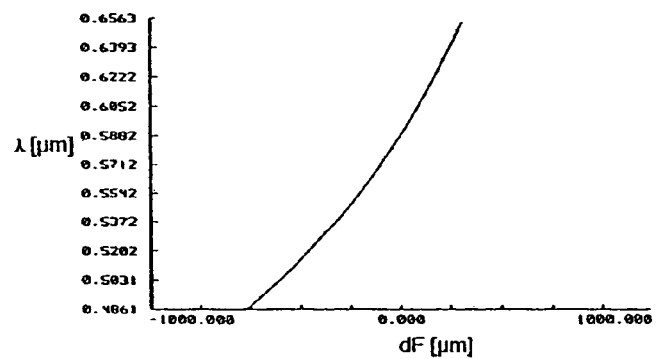
FIG. 8 shows a diagram illustrating the chromatic longitudinal aberration of focusing optics in the movement-determining device in FIG. 7.

By way of example, FIG. 8 shows the dispersion of strongly dispersive focusing optics 41 in the form of a diagram, in which the wavelength λ is shown as a function of the change dF of the focus position.

Figure 9:
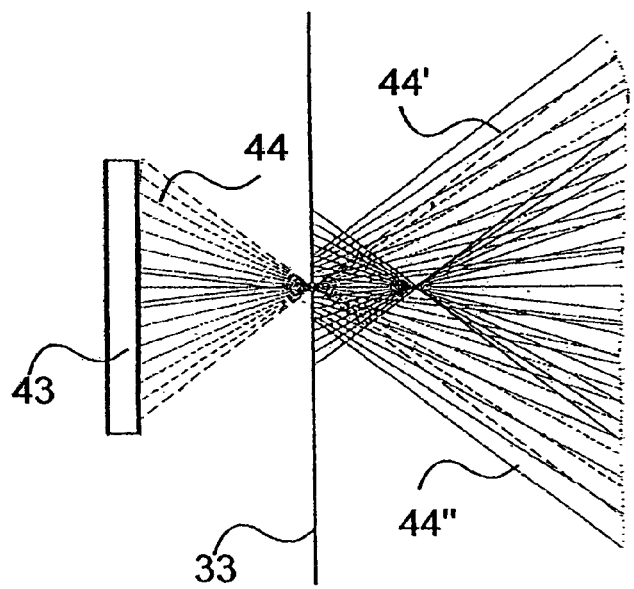
FIG. 9 shows a schematic view of focus positions near a small-aperture stop of the movement-determining device in FIG. 7.

In this manner, for fixed positions of the illumination and focusing optics 31 and 41, respectively, a different object plane conjugated with the aperture of the aperture stop 33 is obtained for each wavelength, from which object plane an illuminated spot 15 of the corresponding wavelength can be imaged onto the aperture stop 33. Conversely, an object in a plane is imaged, as a function of the wavelength, into different conjugated planes in the region of the aperture stop 33. This is shown in FIG. 9 for partial light beams 44, 44' and 44" of the illumination ray bundle 13, the foci of said partial light beams being spaced apart along the direction of the detection ray bundle 14. Only if the focus of the part 44 of the illumination ray bundle 13 reflected by the cornea is imaged into the aperture of the aperture stop 33 can a part of the detection ray bundle which is sufficient for detection reach the photodetector 43. Other portions are suppressed.

Figure 7:
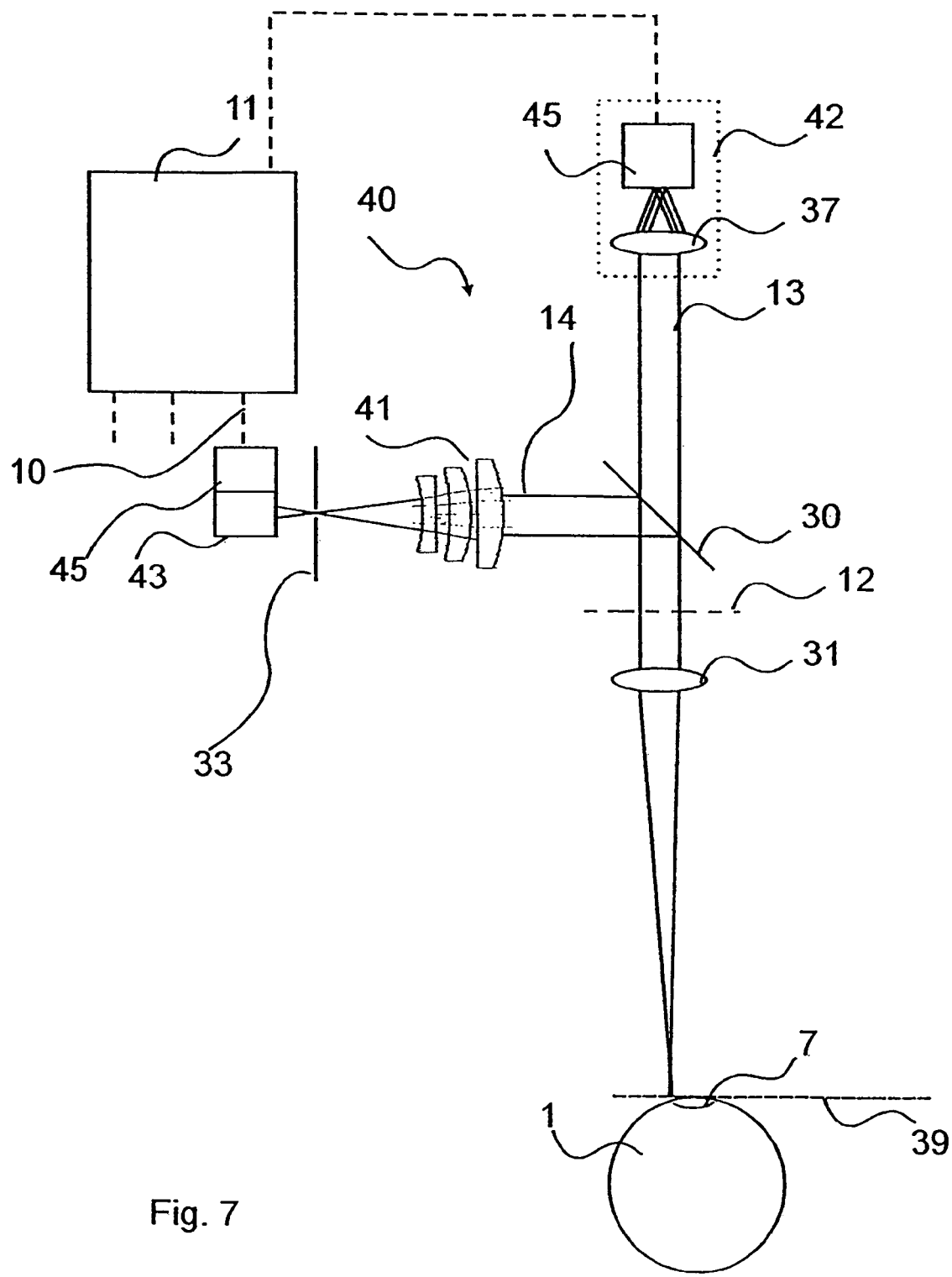
FIG. 7 shows a schematic view of an eye and of part of a movement-determining device according to a fourth embodiment.

In order to allow use of this property, the illumination unit 42 is used, which, in contrast to the illumination unit 29 comprises light-emitting diodes for red, green and blue light as well as a control circuit by means of which the different light emitting diodes are sequentially switched on in an alternating manner according to a predetermined time program. The light emitting diodes and the control circuit are shown in FIG. 7 by a rectangle 45 only very schematically. In each switching operation, the control circuit outputs a corresponding color signal via a connection to a detection circuit 46 which replaces the detection circuit 35.

The photodetector 43 has substantially the same sensitivity to optical radiation that can be emitted by the illumination unit 42. As an alternative, wavelength-dependent changes in sensitivity can be corrected by calibration and by the use of calibrating factors (which are suitably stored).

A distance-determining unit in the sense of the invention is thus provided by the semi-transmitting mirror 30, the illumination optics 31, the focusing optics 41, the small-aperture stop 33, the photodetector 43 and the detection circuit 46.

Now, during operation, illumination ray bundles 13 are irradiated on the cornea 7, alternating between red, green and blue light, and are focused in the region of the cornea 7. Thus, every time the color changes, a corresponding color signal is output to the detection circuit 46.

The illuminated spot 15 formed on the cornea 7 is then imaged by means of the detection optics, which comprise the illumination optics 31, the semi-transmitting mirror 30 and the focusing optics 41. The detection ray bundle 14 can only pass through the aperture stop 33 if, at the wavelength presently used, the focus of the illumination ray bundle 13 reflected by the cornea 7 is located in an object plane which is conjugated with the aperture of the aperture stop 33.

Upon detection of a signal from the photodetector 43, the detection circuit 46 transforms a simultaneously received color signal from the illumination unit 42 into a distance signal, which results from the focal position at the wavelength presently used. The distance signal is formed by comparing the individual signals.

A movement-determining device according to a fifth embodiment differs from the movement-determining device according to the third embodiment in the design of the sensing units. Otherwise, it is identical in structure and is connected to the treatment unit 5. Further, the illumination units of the sensing units represent illumination units of the movement-determining device in this case, too. Therefore, the same reference numerals are used for identical or analogous components, and the corresponding statements also apply here.

Figure 10:
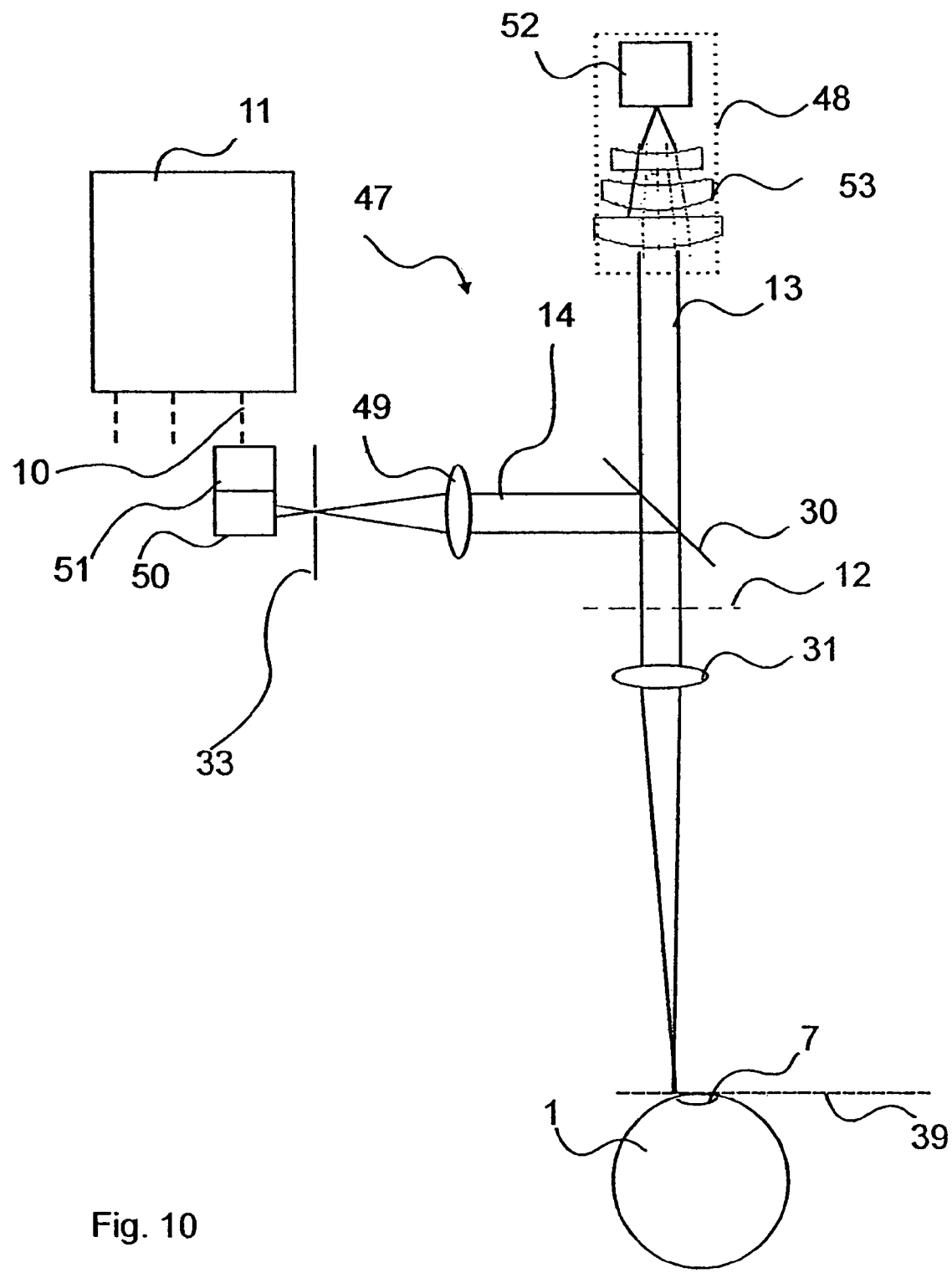
FIG. 10 shows a schematic view of an eye and of part of a movement-determining device according to a fifth embodiment, FIG. 11 a schematic view of focus positions of illumination ray bundles of the movement-determining device in FIG. 8 near the cornea of the eye.
Figure 12:
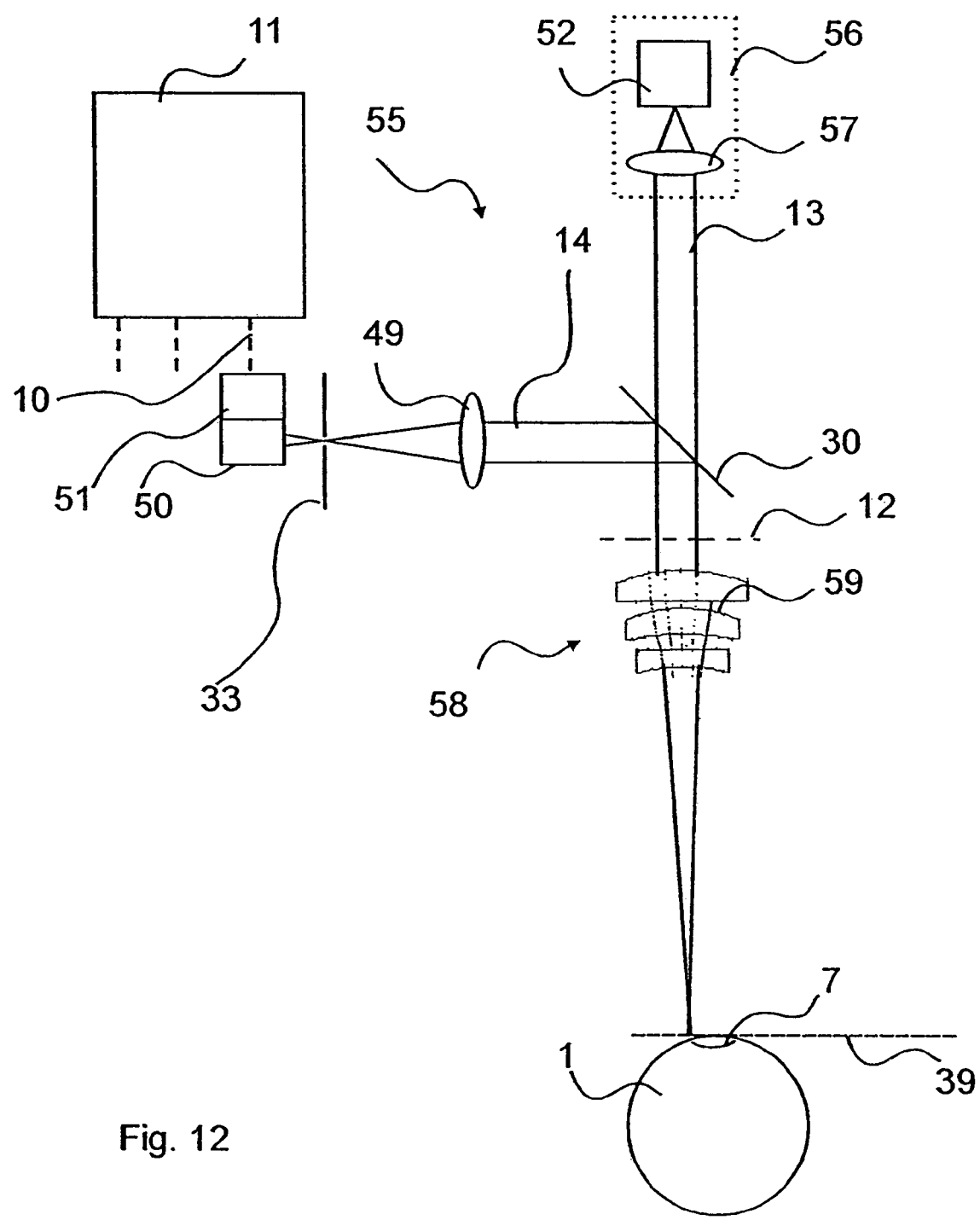
FIG. 12 shows a schematic view of an eye and of part of a movement-determining device according to a sixth embodiment.

The identically provided sensing units 47, one of which is shown in FIG. 10, each differ from the sensing units of the third embodiment by a modified illumination unit 48, color-corrected focusing optics 49, a three-channel spectrometer 50 which replaces the photodetector 34 and a modified detection circuit 51.

As the source of radiation, the illumination unit 48 now comprises a continuously operating white-light source and ray bundle forming optics 53, which have marked longitudinal chromatic aberrations (also referred to herein as "strongly dispersive").

Figure 11:
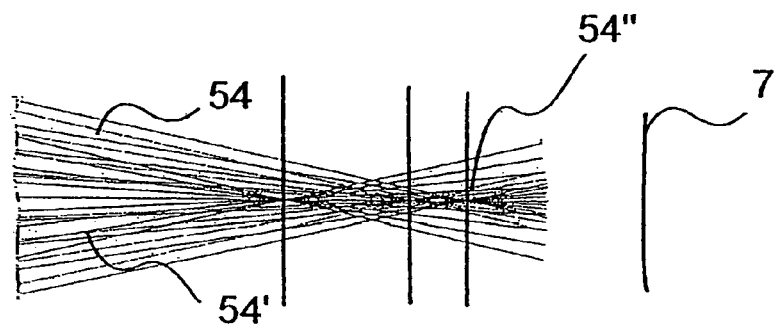

By use of the ray bundle forming optics 53 having a marked longitudinal chromatic aberration, the illumination ray bundle 13 is focused in the region of the cornea, as a function of the respective wavelength, in different planes in the region of the cornea which are offset in the direction of the illumination ray bundle 13. This is illustrated in FIG. 11 wherein the focal positions in front of the cornea 7 are shown for three partial ray bundles 54, 54' and 54" in the colors of red, green and blue, respectively. While the focus for the blue light is located closest to the illumination optics 31, that for the green light is shifted towards the cornea 7 and that for the red light is shifted even more in that direction.

The detection optics now comprise the color-corrected illumination optics 31, the semi-transmitting mirror 30 and the color-corrected focusing optics 49, so that now the object plane 39, which is conjugated with the plane of the aperture stop 33, occupies a position which is substantially identical and fixed for the wavelengths of use.

A significant part of the detection ray bundle 14 of one wavelength can only pass through the aperture stop 33 if the corresponding focus of the illumination ray bundle 13 reflected by the cornea 7 is located close to or on the object plane 39 conjugated with the plane of the aperture stop 33 relative to the detection optics.

The three-channel spectrometer 50 receives, in a temporally resolved manner and at a predetermined detection frequency (e.g. 10 kHz), the ray bundle passed through the aperture stop 33 and outputs one signal each for the red, green, and blue channels to the detection circuit 51. Said spectrometer may be structured as a color splitter cascade with respectively associated photo receivers or, for example, as a photodiode line, wherein each element of the line has another color filter overlying it.

According to the detection frequency, the detection circuit 51 determines a distance of the cornea 7 from the reference plane, on the basis of the intensities received in the three channels and the dispersive properties of the ray bundle forming optics 53 or the wavelength-dependent position of the foci of the illumination ray bundle 13 reflected by the cornea, respectively, and outputs a corresponding distance signal to the evaluating means 11.

The semi-transmitting mirror 30, the illumination optics 31, the focusing optics 49, the small-aperture stop 33, the spectrometer 50 and the detection circuit 51 form a distance-determining unit.

A movement-determining device according to a sixth embodiment differs from the movement-determining device according to the fifth embodiment in the design of the sensing units. Otherwise, it is identical in structure and is connected to the treatment unit 5. Therefore, the same reference numerals are used for identical or analogous components, and the corresponding statements also apply here.

The sensing units 55 differ from the sensing units 47 of the fifth embodiment by the provision of the illumination unit 56, which still comprises the white-light source 52, but now includes color-corrected ray bundle forming optics 57, and the illumination optics 58, which comprise a strongly dispersive objective 59 having a dispersion similar to that shown in FIG. 8.

Since the illumination optics 58 and, in particular, the strongly dispersive objective 59 are also part of the detection beam path, the dispersive effects described in connection with the fourth and fifth embodiment add up to each other. This results in a better spatial separation of the foci for different wavelengths, thus improving the accuracy of the distance determination.

At the same time, as described in the previous embodiment, a very high sensing speed is achieved, because the temporal resolution is practically limited only by the sensing speed of the spectrometer 50.

Otherwise, the sensing unit is identical in operation to that of the fifth embodiment, except that the distance signal is determined taking into account the dispersive effects in the illumination and detection beam paths.

The invention claimed is:

1. A device for determining a movement of an eye, comprising:

an illumination unit, which generates optical radiation during operation and emits it as an illumination ray bundle for illumination of at least one region on the cornea of the eye;

a distance-determining unit, which senses, in a temporally resolved manner, the illumination ray bundle returned by the cornea as a detection ray bundle and generates a distance signal using the received optical radiation of the detection ray bundle, said signal corresponding to a distance of the cornea from a reference plane, which is defined relative to the distance-determining unit; and an evaluating unit which, using said distance signal, generates a position or movement signal corresponding to a position or movement of the eye;

illumination optics for focusing the illumination ray bundle for at least one wavelength in a predetermined range of possible positions of the cornea; and wherein the distance-determining unit performs confocal imaging and comprises:

detection optics, a small-aperture stop arranged following said detection optics and located in a stop plane, and a detection unit arranged following said aperture stop for detecting a part of the detection ray bundle having passed the small-aperture stop, wherein the stop plane is conjugated with an object plane associated with the wavelength, said object plane being located in a range of possible positions of the cornea.

2. The device as claimed in claim 1, wherein the illumination unit is provided such that a diameter of the illumination ray bundle on the cornea of the eye arranged in front of the device is between 2 μm and 20 μm during operation.

3. The device as claimed in claim 1, wherein the position of the illumination and/or detection optics and/or of the aperture stop and/or the focal length of the illumination and/or detection optics and/or the position of the illuminated spot can be changed by means of a drive.

4. The device as claimed in claim 1, wherein optical radiation of different wavelengths can be emitted by the illumination unit, and ray bundle forming optics of the illumination unit, the illumination optics and/or the detection optics are dispersive by a predetermined degree.

5. The device as claimed in claim 1, wherein the illumination unit emits optical radiation in at least two different spectral ranges.

6. The device as claimed in claim 1, wherein the illumination unit comprises a source of radiation for emitting optical radiation in a predetermined spectral range.

7. The device as claimed in claim 1, wherein the detection detects the part of the detection ray bundle having passed the small-aperture stop.

8. The device as claimed in claim 5, wherein the detection unit detects part of the detection ray bundle having passed behind the small-aperture stop in a manner timed with the change of the spectral ranges of the illumination ray bundles.

9. The device as claimed in claim 1, wherein the illumination optics and the detection optics share a common objective.

10. The device as claimed in claim 9, wherein the common objective has a predetermined longitudinal chromatic aberration above the Rayleigh length of the illumination ray bundle.

11. The device as claimed in claim 1, comprising at least one illumination unit, which emits two illumination ray bundles and which illuminates two different areas on the cornea of the eye, and comprising at least one distance-determining unit, which receives, in a temporally resolved manner, detection ray bundles reflected by said two areas on the cornea and generates distance signals corresponding to distances of the cornea from two reference planes, said reference planes each being defined for one of the detection ray bundles relative to the distance-determining unit and the evaluating unit evaluating the distance signals and generating position or movement signals which correspond to a position or movement of the eye in two spatial directions.

12. The device as claimed in claim 1, comprising at least one illumination unit, which emits three illumination ray bundles, which illuminate three different areas forming the corners of a triangle on the cornea of the eye, and comprising at least one distance-determining unit, which receives, in a temporally resolved manner, detection ray bundles reflected by said three areas on the cornea and generates distance signals corresponding to distances of the cornea from three reference planes, said reference planes each being defined for one of the detection ray bundles relative to the distance-determining unit and the evaluating unit evaluating the distance signals and generating position or movement signals which correspond to a position or movement of the eye in three spatial directions.

13. A method of determining a movement of an eye comprising the steps of:

radiating optical radiation from an illumination unit onto at least one region on the cornea of the eye as an illumination ray bundle;

generating distance signals with a distance-determining unit, the distance signals corresponding to the distance of the cornea from a predetermined reference plane defined relative to the distance-determining unit in a temporally resolved manner, using optical radiation from the illumination bundle returned by the cornea as detection ray bundles;

generating position or movement signals corresponding to a position or movement of the eye from the distance signals with an evaluating unit;

focusing the illumination ray bundle for at least one wavelength into a predetermined range of possible positions of the cornea with illumination optics;

performing confocal imaging by focusing the detection ray bundle through detection optics of the distance determining unit into a region of a small-aperture stop located in a stop plane following the detection optics, said stop plane being conjugated with an object plane which is associated with the wavelength and which lies in a predetermined range of possible positions of the cornea;

detecting part of the detection ray bundle that passes the small-aperture stop with a detection unit; and generating the distance signal by detection of the optical radiation passing through the small-aperture stop.

14. The method as claimed in claim 13, wherein the illumination ray bundle has a diameter of between 2 μm and 20 μm at the cornea.

15. The method as claimed in claim 13, wherein the range of possible distances of the cornea from the reference plane is scanned by changing the distance between the object plane and the small-aperture stop.

16. The method as claimed in claim 13, wherein optical radiation of different wavelengths is used, and the illumination and/or detection ray bundle is guided through at least one strongly dispersive optical functional element.

17. The method as claimed in claim 13, wherein illumination ray bundles with optical radiation in at least two different spectral ranges are alternately used in a predetermined time sequence.

18. The method as claimed in claim 13, wherein the illumination ray bundle comprises optical radiation in a spectral range of 400 nm to 1700 nm.

19. The method as claimed in claim 16, wherein the intensity of the detection ray bundle behind the small-aperture stop is detected in a spectrally and temporally resolved manner.

20. The method as claimed in claim 17, wherein the intensity of the detection ray bundle behind the small-aperture stop is detected in a manner timed with the change of the spectral ranges of the illumination ray bundles.

21. The method as claimed in claim 13, wherein the illumination ray bundle is radiated onto an area of the cornea at an angle of incidence of less than ten degrees.

22. The method as claimed in claim 13, wherein the illumination ray bundle is radiated onto an area of the cornea at an angle of incidence of less than five degrees.

23. The method as claimed in claim 13, further comprising the step of illuminating at least two different areas on the cornea by at least two different illumination ray bundles;
   generating distance signals relating to the distances of the cornea from corresponding predetermined reference planes in a temporally resolved manner, using the optical radiation respectively returned by the cornea as detection ray bundles; and
   generating position or movement signals relating to a position or movement of the eye in at least two spatial directions on the basis of said distance signals.

24. The method as claimed in claim 13, further comprising the steps of:
   illuminating at least three different areas on the cornea forming corners of a triangle by at least three different illumination ray bundles;
   generating distance signals relating to the distances of the cornea from corresponding, predetermined reference planes in a temporally resolved manner, using the optical radiation respectively returned by the cornea as detection ray bundles; and
   generating position or movement signals relating to a position or movement of the eye in at least three spatial directions on the basis of said distance signals.

25. The method as claimed in claim 13, further comprising the steps of guiding illumination and detection radiation over the eye synchronously with a therapeutic beam.

26. A device for determining a position of an element of an eye, comprising:
   an illumination unit, which generates optical radiation during operation and emits it as an illumination ray bundle for illumination of at least one region on the element of the eye;
   a distance-determining unit, which senses, in a temporally resolved manner, the illumination ray bundle returned by the element of the eye as a detection ray bundle and generates a distance signal using the received optical radiation of the detection ray bundle, said distance signal corresponding to a distance of the element of the eye from a reference plane, which is defined relative to the distance-determining unit;
   an evaluating unit which, using said distance signal, generates a position signal corresponding to the position of the element of the eye, and
   illumination optics for focusing the illumination ray bundle for at least one wavelength in a predetermined range of possible positions of the element of the eye and wherein the distance-determining unit performs confocal imaging and comprises detection optics, a small-aperture stop arranged following said detection optics and located in a stop plane, and a detection unit arranged following said aperture stop for detecting a part of the detection ray bundle having passed the small-aperture stop, wherein the stop plane is conjugated with an object plane associated with the wavelength, said object plane being located in a range of possible positions of the cornea;
   wherein the detection unit detects the part of the detection ray bundle having passed the small-aperture stop spectrally and temporally resolved; and
   wherein the detection unit detects the part of the detection ray bundle having passed the small-aperture stop in a manner timed with the change of the spectral ranges of the illumination ray bundles.

27. The device as claimed in claim 26, wherein the position of the illumination and/or detection optics and/or of the aperture stop and/or the focal length of the illumination and/or detection optics and/or the position of the illuminated spot can be changed by means of a drive.

28. A device for determining a position of an element of an eye, comprising:
   an illumination unit, which generates optical radiation during operation and emits it as an illumination ray bundle for illumination of at least one region on the element of the eye;
   a distance-determining unit, which senses, in a temporally resolved manner, the illumination ray bundle returned by the element of the eye as a detection ray bundle and generates a distance signal using the received optical radiation of the detection ray bundle, said distance signal corresponding to a distance of the element of the eye from a reference plane, which is defined relative to the distance-determining unit;
   an evaluating unit which, using said distance signal, generates a position signal corresponding to the position of the element of the eye, and
   illumination optics for focusing the illumination ray bundle for at least one wavelength in a predetermined range of possible positions of the element of the eye and wherein the distance-determining unit performs confocal imaging and comprises detection optics, a small-aperture stop arranged following said detection optics and located in a stop plane, and a detection unit arranged following said aperture stop for detecting a part of the detection ray bundle having passed the small-aperture stop, wherein the stop plane is conjugated with an object plane associated with the wavelength, said object plane being located in a range of possible positions of the cornea;
   wherein optical radiation of different wavelengths can be emitted by the illumination unit, and ray bundle forming optics of the illumination unit, the illumination optics and/or the detection optics are dispersive by a predetermined degree; and
   wherein the illumination optics and the detection optics share a common objective; and
   wherein the common objective has a predetermined longitudinal chromatic aberration above the Rayleigh length of the illumination ray bundle.

29. The device as claimed in claim 26, wherein the illumination unit emits optical radiation in at least two different spectral ranges.

30. The device as claimed in claim 26, wherein the illumination unit comprises a source of radiation for emitting optical radiation in a predetermined spectral range.

* * * * *

UNITED STATES PATENT AND TRADEMARK OFFICE
CERTIFICATE OF CORRECTION

PATENT NO. : 7,784,944 B2
APPLICATION NO. : 10/560475
DATED : August 31, 2010
INVENTOR(S) : Dirk Mühlhoff et al.

Page 1 of 1

It is certified that error appears in the above-identified patent and that said Letters Patent is hereby corrected as shown below:

On the Title page of the patent under item (75) Inventors: it should read as follows:

Dirk Mühlhoff, Kunitz (DE); Mario Gerlach, Hohen Neuendorf (DE)

Signed and Sealed this
Thirtieth Day of April, 2013

Teresa Stanek Rea
*Acting Director of the United States Patent and Trademark Office*